United States Patent
Nordquist et al.

(12)

(10) Patent No.: US 6,756,363 B1
(45) Date of Patent: Jun. 29, 2004

(54) SOLUTIONS AND FILMS OF GLYCATED CHITOSAN

(75) Inventors: Robert E. Nordquist, Oklahoma City, OK (US); Raoul Carubelli, Oklahoma City, OK (US)

(73) Assignee: Wound Healing of Oklahoma, Inc., Oklahoma City, OK (US)

( * ) Notice: Subject to any disclaimer, the term of this patent is extended or adjusted under 35 U.S.C. 154(b) by 148 days.

(21) Appl. No.: 09/715,429

(22) Filed: Nov. 17, 2000

(51) Int. Cl.$^7$ .................. A61K 31/722; C08B 37/08
(52) U.S. Cl. ........................... 514/55; 536/20
(58) Field of Search .............. 514/55; 536/20

(56) References Cited

U.S. PATENT DOCUMENTS

| | | | |
|---|---|---|---|
| 4,141,973 A | 2/1979 | Balazs | 424/180 |
| 4,424,346 A | 1/1984 | Hall et al. | 536/20 |
| 4,965,253 A | 10/1990 | Goldberg et al. | 514/54 |
| 5,093,319 A | 3/1992 | Higham et al. | 514/55 |
| 5,422,376 A | 6/1995 | Webb | 514/781 |
| 5,510,329 A | 4/1996 | Belkin et al. | 514/12 |
| 5,747,475 A | 5/1998 | Nordquist et al. | 514/55 |
| 6,277,792 B1 | 8/2001 | House | 507/110 |

FOREIGN PATENT DOCUMENTS

| | | | | |
|---|---|---|---|---|
| DE | 198 57 546 A | 6/2000 | | A61K/7/40 |

OTHER PUBLICATIONS

Yalpani M et al: "Unusual rheology of a branched water–soluble chitosan derivative." Nature (London) vol. 302, No. 5911, 1983, pp. 812–814, XP002206892, ISSN: 0028–083.

Patent Abstractsof Japan. vol. 1999, No. 05, May 31, 1999, and JP 11 043441 A (Ichimaru Pharcos Co. Ltd.; Yaizu Suisan Kagaku Kogyo KK; Neetec:KK), Feb. 16, 1999.

Patent Abstractsof Japan. vol. 014, No. 370 (C–0747), Aug. 10, 1990, and JP 02 134310 A (Kao Corp.), May 23, 1990.

Yalpani M et al: "Some chemical and analytical aspects of polysaccharide modifications. 3. Formation of branched–chain, soluble chitosan derivatives." Macromolecules, vol. 17, 1984, pp. 272–281, XP002206891, ISSN: 0024–9297.

*Primary Examiner*—Peter O'Sullivan
(74) *Attorney, Agent, or Firm*—Fellers, Snider, Blankenship, Bailey & Tippens, P.C.

(57) ABSTRACT

Preparations containing glycated chitosan in a physiologically compatible carrier are described. Viscoelastic preparations comprise 1.0–12.0 percent by weight of glycated chitosan in an aqueous solution while lower viscosity solutions possess 0.1–0.5 percent by weight glycated chitosan. The otherwise free amino groups of the chitosan polymer are preferably 30–90% glycated and possess an average molecular weight of between 100,000 and 2,000,000 Daltons, and, most preferably between 100,000 and 1,000,000 Daltons.

14 Claims, No Drawings

SOLUTIONS AND FILMS OF GLYCATED CHITOSAN

BACKGROUND OF THE INVENTION

1. Field of the Invention

This invention relates generally to viscous medical preparations, and, more specifically, to viscous solutions containing glycated chitosan and dried films prepared therefrom.

2. Background

Viscoelastic substances are used routinely in the medical field for protection and manipulation of tissues and maintenance of spaces. Viscoelastic materials prepared from various naturally occurring substances or synthesized in the laboratory include sodium hyaluronate, chondroitin sulfate and combinations thereof, cellulosic materials, and polymers based on acrylamide. Previously used viscoelastics have disadvantages which include allergic reactions, neurotoxic impurities, inadequate viscosity or viscoelasticity; unacceptable levels of particulate materials; gels or bulky polymer chains which might enter and plug fluid meshworks; procurement difficulties due to the use of animal derived raw materials; and excessive cost. Materials which are not broken down and absorbed in vivo also generally require that they be irrigated from the body.

It is thus an object of the present invention to provide improved viscoelastic preparations which are far less subject to the above-noted disadvantages.

SUMMARY OF THE INVENTION

In connection with the present invention there are provided preparations containing glycated chitosan in a physiologically compatible carrier. Such preparations possess useful viscoelastic properties, are absorbable by hydrolysis in vivo and, surprisingly, are endowed with antibacterial qualities. Dry films prepared from glycated chitosan solutions are also provided.

Chitosan is a deacetylated derivative of chitin, a plentiful substance readily isolated from the shells of crustaceans such as crab, lobster and shrimp. Glycated chitosan refers to products resulting from the reaction between free amino groups of chitosan and carbonyl groups of reducing monosaccharides and/or oligosaccharides.

The preferred viscoelastic preparations comprise 1.0–12.0 percent by weight of glycated chitosan in an aqueous solution, depending upon the desired physical properties. The otherwise free amino groups of the chitosan polymer are preferably 30–90% glycated, and the molecules possess an average molecular weight of between 100,000 and 2,000,000 Daltons, and, most preferably between 100,000 and 1,000,000 Daltons. The inventive viscoelastic solutions are of a viscosity greater than 10,000 centistokes (one centistoke=a resistance to flow of 1 mm/sec) and, most preferably between 10,000 and 80,000 centistokes, measured at 25° C. A particularly preferred form of glycated chitosan for use in the inventive preparations is galacto-chitosan.

The inventive solutions and films are useful in a myriad of medical applications, including, for example, as viscoelastic ophthalmic agents and as drug carriers for medicaments for topical application to the eye; antimicrobial coatings for use on adhesive strips or burn and wound dressings; tissue void replacement materials; lavage solutions; tissue separation films, mouth rinses; facial lotions; or as hand and body disinfectants.

In an alternate embodiment, certain low viscosity preparations are provided for use as ophthalmic wetting agents for topical application to the eye and as drug carriers for medicaments for topical application to the eye. The preparations are particularly useful when combined with certain medicaments or drugs, which are entrapped in the glycated chitosan preparations. Since the preparations are broken down over time by enzymes in eye secretions, they have the characteristic of sustained release. For use as a wetting agent or eye drop, the inventive preparations comprise less than 1.0, and preferably 0.1–0.5, percent by weight of glycated chitosan in a physiologically compatible aqueous solution, while possessing 30–90%, preferably 60%, glycation of the otherwise free amino groups of the chitosan polymer and having a viscosity in the range from about 10 centistokes to about 100 centistokes.

Especially for ophthalmic preparations, the glycated chitosan is preferably contained in an aqueous solution having a pH between 5.5 and 7.5, and, most preferably, in a dilute slightly acidic aqueous solution having a pH between 6.3 and 7.

A better understanding of the present invention, its several aspects, and its objects and advantages will become apparent to those skilled in the art from the following detailed description, wherein there is described the preferred embodiment of the invention, simply by way of illustration of the best mode contemplated for carrying out the invention.

DETAILED DESCRIPTION OF THE PREFERRED EMBODIMENT

Before explaining the present invention in detail, it is important to understand that the invention is not limited in its application to the details of the particular preparations and the steps described herein. The invention is capable of other embodiments and of being practiced or carried out in a variety of ways. It is to be understood that the phraseology and terminology employed herein is for the purpose of description and not limitation.

Chitin is a linear homopolymer composed of N-acetylglucosamine units joined by β1→4 glycosidic bonds. Chitin and chitosan (resulting from various degrees of deacetylation of chitin), and their derivatives, are endowed with interesting chemical and biological properties that have led to a varied and expanding number of industrial and medical applications, including their use in connection with bandages and sutures, burn dressings, skin substitutes, bone and dental prostheses, food packaging, drug encapsulation, cosmetics, metal chelation and associated antioxidant effects, waste water treatment, hemostasis, anticoagulants (after sulfation), and dye doping, among other things.

Solubilization of chitin and chitosan has been achieved by partial hydrolysis to shorten the length of their molecules. For chitosan, treatment with a variety of acids, both organic and inorganic, leads to the formation of water soluble chitosonium salts by protonation of the free amino groups. Additional modifications of the amino groups include the introduction of chemical groups such as carboxymethyl, glyceryl, N-hydroxybutyl and others. U.S. Pat. No. 5,093,319, incorporated herein by reference, describes the use of chitin and chitosan derived polymers such as chitosan acetate; chitosan lactate; chitosan sulfate; chitosan glutamate; methyl-chitosan; N-carboxyl methyl-chitosan; O-carboxyl methyl-chitosan; N,O-carboxyl ethyl-chitosan; N-carboxyl ethyl-chitosan; O, carboxyl ethyl-chitosan; N,O- carboxyl propyl-chitosan; N-carboxyl propyl chitosan; O-carboxyl ethyl chitosan; cross-linked chitosan or derivatives thereof, and carboxyl alkyl chitins such as carboxymethyl chitin, carboxyethyl chitin and carboxypropyl chitin in a viscoelastic form for in vivo use as a biodegradable adhesion preventative.

Glycated chitosan was first described in U.S. Pat. No. 5,747,475, incorporated herein by reference, as an immunoadjuvant in connection with laser/sensitizer assisted immunotherapy for cancer. (See Cols. 8–18 of the '475 patent). Glycated chitosan is a product of the glycation (i.e., non-enzymatic glycosylation) of free amino groups of chitosan, followed by stabilization by reduction. Glycation endows the chitosan with advantageous solubility characteristics which facilitated the use of this chitosan derivative in conjunction with laser/sensitizer assisted immunotherapy. The glycation of chitosan also renders the chitosan more hydrophilic whereby more water is absorbed and retained by the polymer than would otherwise be the case.

The products resulting from the reaction between free amino groups of chitosan and carbonyl groups of reducing monosaccharides and/or oligosaccharides (ie., glycated chitosan) are mainly a mixture of Schiff bases, i.e. the carbon atom of the initial carbonyl group double bonded to the nitrogen atom of the amino group, and Amadori products, i.e. the carbon atom of the initial carbonyl group bonded to the nitrogen atom of said amino group by a single bond while an adjacent carbon atom is double bonded to an oxygen atom forming a ketone group. The products may be used as such or after stabilization by reduction with hydrides, such as sodium borohydride, or by exposure to hydrogen in the presence of suitable catalysts. The galactose derivative of chitosan is particularly preferred insofar as galactose has a relatively high naturally occurring incidence of its open chain form. The glycated chitosan may be initially prepared in a powder form, as a viscous solution, or in other forms. But as used in connection with the inventive preparations herein, the glycated chitosan is in aqueous solution or is dried into a thin film from such an aqueous solution.

Preparation of Glycated Chitosan

Glycated chitosan may be obtained by reacting chitosan with a stoichiometric excess of a monosaccharide and/or oligosaccharide, preferably in the presence of an acidifying agent, for a time sufficient to accomplish Schiff base formation between the carbonyl group of the sugar and the primary amino groups of chitosan (also referred to herein as glycation of the amino group) to a degree whereby a 30–90% (and most preferably 60%) glycation of the chitosan polymer is achieved. As mentioned above, this may be, and is preferably, followed by stabilization by reduction of Schiff bases and of their rearranged derivatives (Amadori products). The molecular weight of the polymers preferred for use in the present invention most preferably range from 100,000 to 1,000,000 Daltons. NMR tracings can be used to verify the bonding of the monosaccharides and/or oligosaccharides to the chitosan polymer, whereas chemical measurement of remaining free amino groups, such as via a ninhydrine reaction, can be used to assess the degree of glycation.

The inventive solutions contain glycated chitosan in a physiologically compatible carrier. "Physiologically compatible" is employed to refer to materials which, when in contact with tissues in the body, are not harmful thereto. The term is intended in this context to define, but is not limited to, aqueous solutions which are approximately isotonic with the physiological environment of interest. Non-isotonic solutions sometimes may be clinically useful such as, for example dehydrating agents. Additional components of the inventive solutions may include various salts such as NaCl, KCl, $CaCl_2$, MgCl and Na based buffers. Especially for ophthalmic and viscosurgical preparations, the concentrations of the components of the inventive solutions may be derived to have an osmolality on the order of 250–350 and are buffered to maintain the desired pH of from 5.5 to 7.5. The concentration of the salts and the buffering agents may be chosen to be similar to that of commercially available intraocular irrigating solutions and viscoelastic surgical fluids.

Acceptable manners of preparation of the inventive glycated chitosan solutions and films in accordance with the several aspects of the present invention will be further understood with reference to the following non-limiting examples. The inventive preparations possessing a concentration greater than 1 wt. % glycated chitosan are obtained by concentrating, through dialysis or other means, a 1 wt. % stock. For the low viscosity inventive solutions, a 1 wt. % stock solution is diluted. The viscosity of the inventive solutions may be manipulated by varying either the concentration of the glycated chitosan in solutions, the average molecular weight of the glycated chitosan molecules, or the structure of the glycated chitosan molecule.

EXAMPLE 1

An initial 1 wt. % aqueous solution of glycated chitosan was prepared as follows:

(a) 1 gram of chitosan was added to 100 ml of de-ionized water in a flask and mixed with magnetic stirring until all chitosan was dissolved.

(b) 3 grams of a reducing monosaccharide (e.g., glucose, galactose, ribose), or an equivalent amount of a reducing oligosaccharide, was added to the chitosan solution with gentle stirring. When the suspension is homogeneous, 0.25 ml of toluene was added, and the flask was sealed with aluminum foil. The magnetic stirring continued for 24 hours at room temperature.

(c) After stirring, the suspension was placed in a ventilated fume hood where 1.327 grams of sodium borohydride in 5 ml of 0.1M sodium hydroxide was added in 0.2 ml aliquots (to avoid excessive foaming) to reduce Schiff bases and Amadori products. The solution was then covered loosely with foil, stirred for 10 minutes at room temperature and then 50 minutes in an ice bath.

(d) The flask was removed from the ice bath and the solution was acidified to a pH of 5.5 by the dropwise addition of glacial acetic acid (approximately 1.9 ml) under further magnetic stirring to decompose excess borohydride.

(e) The solution was transferred to a dialysis bag (for example, a SPECTRA/POR #1 membrane obtained from Spectrum Medical Industries, Inc.). The solution was dialyzed against de-ionized water (4 liters×3) refrigerated (4° C.) over a period of 16 hours.

(f) The finished dialysate was transferred to a clean bottle and store in the refrigerator.

EXAMPLE 2

A solid weight determination may be made by transferring approximately 5.0 ml of the glycated chitosan (GC) solution to a polystyrene weighing boat and placing it in a convection oven (temperature set at 60° C.) for drying (which occurs in approximately 30 minutes). Record the following:

|  | Grams |
| --- | --- |
| Weighing Boat (WB) | |
| WB + GC Solution, before drying | |
| WB + GC Solution, after drying | |

The percent solid weight of GC in the solution is calculated as follows:

$$\frac{(WB + GC\ solid) - (WB)}{(WB + GC\ Solution) - (WB)} \times 100\%$$

EXAMPLE 3

For use, the GC solution may be sterilized. To achieve sterilization, quantities of the GC solution are placed in amber serum bottles which are capped with butyl stoppers and sealed with an aluminum seal. The bottles are then transferred to an autoclave, wherein the temperature is set to approximately 121° C. Sterilization is achieved in about 5 minutes. Once the bottles have cooled to room temperature, the GC solution is ready for use.

EXAMPLE 4

Particularly preferred for use in connection with the present invention is galacto-chitosan. The structure of galacto-chitosan and the preparation of galacto-chitosan from chitosan and D-galactose by reductive amination is shown diagrammatically below to further illustrate the best mode for preparing the most preferred form of glycated chitosan:

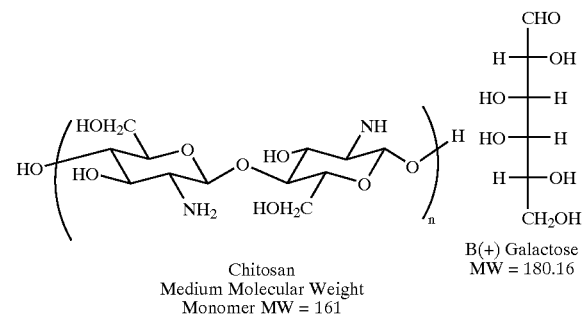

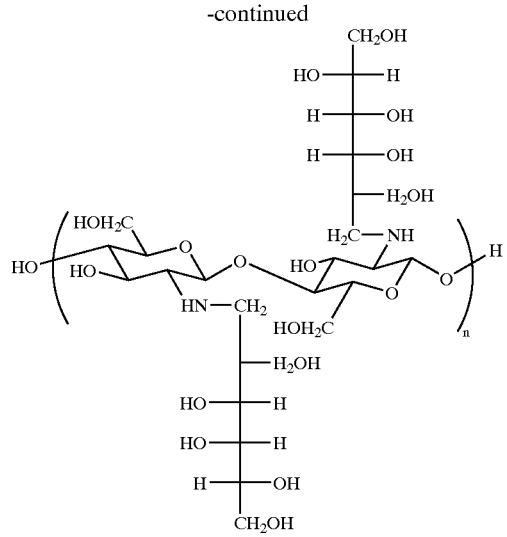

EXAMPLE 5

Various solutions of galacto-chitosan were prepared in accordance with the steps of Example 1 using as a source of chitosan PROTASAN UP CL110 (chitosan chloride) obtained from Pronova Biopolymer which possesses approximately 87% deacetylation and is of an average molecular weight of about 111,000 Daltons.

Example 5A

A solution was prepared wherein 30% of the free amino groups of the chitosan molecules (i.e., 30% of the 87%) were glycated with galactose. The resulting galacto-chitosan product possessed an average molecular weight of 128,130 Daltons.

Example 5B

A solution was prepared wherein 60% of the free amino groups of the chitosan molecules were glycated with galactose. The resulting galacto-chitosan product possessed an average molecular weight of 146,766 Daltons.

Example 5C

A solution was prepared wherein 90% of the free amino groups of the chitosan molecules were glycated with galactose. The resulting galacto-chitosan product possessed an average molecular weight of 165,181 Daltons.

EXAMPLE 6

Various solutions of galacto-chitosan were prepared in accordance with the steps of Example 1 using as a source of chitosan a 21.4% deacetylated chitosan product (FLUKA Medium) obtained from Sigma-Aldrich Co. which is of an average molecular weight of about 750,000 Daltons.

Example 6A

A solution was prepared wherein 30% of the free amino groups of the chitosan molecules (i.e., 30% of the 21.4%) were glycated with galactose. The resulting galacto-chitosan product possessed an average molecular weight of 780,038 Daltons.

Example 6B

A solution was prepared wherein 60% of the free amino groups of the chitosan molecules were glycated with galactose. The resulting galacto-chitosan product possessed an average molecular weight of 809,660 Daltons.

Example 6C

A solution was prepared wherein 90% of the free amino groups of the chitosan molecules were glycated with galactose. The resulting galacto-chitosan product possessed an average molecular weight of 839,647 Daltons.

Soluble forms of glycated chitosan may be used individually or in combination, both as such and/or after additional chemical or enzymatic modification. These modifications may include, but are not limited to, the generation of reactive groups such as carbonyls and carboxyl groups on the substituents introduced by glycation.

Aldehydes may be generated by oxidation of the carbohydrate side chain (e.g. treatment with periodate or lead tetraaceate) or, for example, the enzymatic oxidation of the primary alcohol group of galactosyl residues with galactose oxidase.

Oxidation of the aldehyde groups (e.g. by treatment with hypohalites) may be utilized to obtain the carboxylic acid derivatives. Alternatively, bifunctional compounds containing both free carbonyl and carboxylic groups (e.g. uronic acids) may be utilized during the glycation reaction.

Chitosan deamination with nitrous acid generates reducing aldoses and oligosaccharides suitable for the glycation of chitosan. Deamination of the deacetylated glucosaminyl residues by nitrous acid results in the selective cleavage of their glycosidic bonds with the formation of 2,5-anhydro-D-mannose residues.- Depending on the composition of specific areas of the chitosan chain, the anhydro hexose could be released as the monosaccharide, or occupy the reducing end of an oligosaccharide. Release of free N-acetylglucosamine could also occur from some regions of the chitosan chain. Similar treatment of N-deacetylated glycoproteins and glycolipids can be utilized to obtain oligosaccharides of defined chemical composition and biological activity for special preparations of glycated chitosan. This includes normal as well as pathological glycoconjugates.

The various products obtained by chemical or enzymatic modification of chitosan glycation may be reacted with other natural or synthetic materials, e.g., reaction of aldehyde-containing derivatives of glycated chitosan with substances containing free amino groups, such as on the side chains of amino acids or proteins rich in lysine residues such as in collagen, on hexosamine residues as in chitosan and deacetylated glycoconjugates, or on natural and synthetic amines and polyamines. With di- and poly amines this is expected to generate crosslinking through Schiff base formation and subsequent rearrangements, condensation, dehydration, etc.

Stabilization of modified glycated chitosan materials can be made by chemical reduction or by curing involving rearrangements, condensation or dehydration, either spontaneous or by incubation under various conditions of temperature, humidity and pressure.

The chemistry of Amadori reaarangements, Schiff bases and the Leukart-Wallach reaction is detailed in *The Merck Index*, Ninth Edition (1976) pp. ONR-3, ONR-55 and ONR-80, Library of Congress Card No. 76-2723 1, the same being incorporated herein by reference. The chemistry of nucleophilic addition reactions as applicable to the present invention is detailed in Chapter 19 of Morrison and Boyd, *Organic Chemistry*, Second Edition (eighth printing 1970), Library of Congress Card No. 66-25695, the same being incorporated herein by reference.

The preferred viscoelastic solutions having greater than 1 wt. % glycated chitosan are especially useful as a tissue void replacement material, such as for ophthalmic surgery, and as a lavage solution for preventing abdominal adhesions following surgery. In a particularly preferred aspect of the invention, a 9 wt. % aqueous solution of glycated chitosan of a viscosity of about 77,000 centistokes is provided for these purposes. In these applications, the inventive solutions satisfy the need for a lightweight material for filling tissue voids while providing protection to tissues and contributing to hemostasis.

It will also be understood by those skilled in the art that the inventive viscosurgical preparations may be used in admixture with other viscosurgical materials. For example, the invention glycated chitosan solutions are compatible with hyaluronic acid, chondroitin sulfate and CMC, whereby mixtures possessing desirable combinations of rheology, stability and biocompatibility may be achieved.

On the other hand, low viscosity solutions of glycated chitosan, i.e., of a concentration less than 1.0 weight percent, and preferably between 0.1 and 0.5 wt. %, and having a viscosity of between about 10 and 100 centistokes, have application as an eye wetting agent/lubricant wherein. The product, being of a relatively high molecular weight, binds to the surface of the eye, is non-toxic, and is absorbable.

In either high or low viscosity solutions, another aspect of the invention is the ability of the inventive solutions to act as a drug or medicament carrier. Drug molecules become entrapped in the glycated chitosan solutions and thereby have the characteristic of sustained release. The inventive solutions may be used effectively for both the prolongation and the control of the effective action of a drug or medicament.

An important and surprising aspect of the invention is the discovery that the inventive preparations of glycated chitosan unexpectedly possess significant antimicrobial activity. The inventive preparations have been tested and proved effective against common strains of bacteria as indicated below:

EXAMPLE 7

For each indicated organism, media plates were inoculated such that a uniform lawn of microorganisms would result. A sample of the inventive preparation was placed on the surface of the media previously inoculated. The plates were incubated for 24–48 hours and examined for zones of inhibition extending beyond the edge of the sample. The samples were removed and the plates re-incubated to determine the viability of the microorganisms under the sample.

| | Zone of Inhibition | |
|---|---|---|
| Organism | Extending Beyond Edge | Beneath Sample |
| *Pseudomones aeruginosa* | not present | no growth |
| *Staph aureus* | not present | no growth |
| *E. coli* | not present | no growth |
| *Candida albicans* | not present | no growth |

While the benefit in connection with the foregoing preparations, the antimicrobial properties of the glycated chitosan opens the door to a host of additional applications. For example, a low cost solution is provided as an antimicrobial coating for adhesive strips and burn or wound dressings. In these applications, the inventive preparations provide the further benefits of hemostasis and an almost infinite shelf life. Inventive solutions may be used to coat or drench appliques or may be applied directly to affected areas in liquid or powder form. In one aspect of the invention, thin films of glycated chitosan are provided which may be incorporated into a wound dressing or which may otherwise be used in medical applications, for example, as a natural polymeric substrate to separate tissues for the prevention of tendon and ligament adhesions after orthopedic surgery and for guided tissue regeneration in dental surgery. Such films may be produced by drying a stock solution of glycated chitosan.

EXAMPLE 8

Small squares of a dry glycated chitosan film were prepared by depositing 10 ml of a 1 wt. % solution of glycated chitosan on a 5 cm×5 cm grid, then drying the preparation in an oven at 57° C.

In other aspects of the invention, the antimicrobial glycated chitosan preparations may be combined with typical ingredients to form cosmetic/hygenic products such as mouth rinses, facial lotions and hand and body disinfectants.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

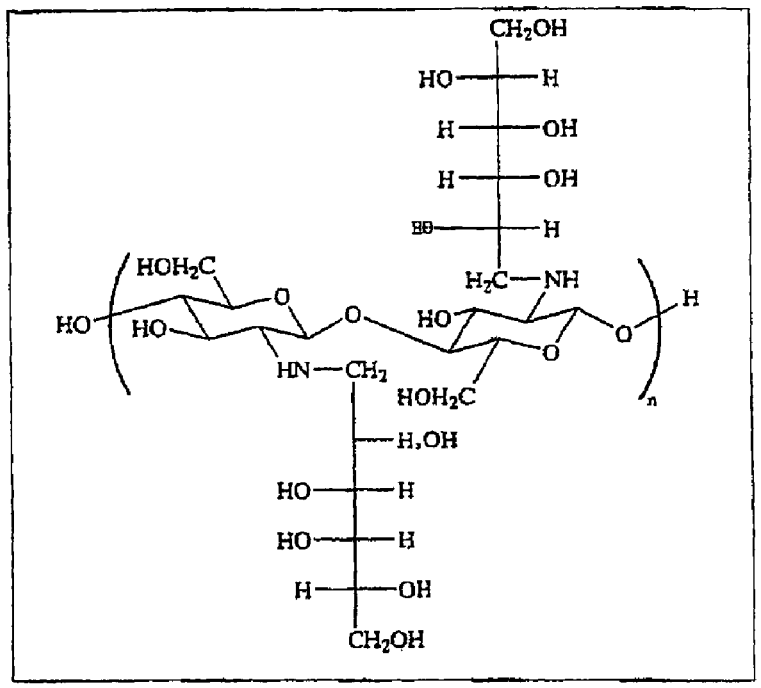

What is claimed is:

1. A viscoelastic preparation comprising greater than 1 percent by weight of a glycated chitosan polymer dispersed in an aqueous solution, said glycated chitosan polymer having a molecular weight of greater than 100,000 Daltons, said aqueous solution having a viscosity greater than 10,000 centistokes measured at 25° C. and a pH in the range of 5.5 to 7.5.

2. The viscoelastic preparation according to claim 1 wherein said aqueous solution possesses a pH between 6.3 and 7.

3. The viscoelastic preparation according to claim 1 wherein said aqueous solution comprises a buffered physiological saline solution of said glycated chitosan.

4. The viscoelastic preparation according to claim 1 wherein said glycated chitosan polymer possesses between 30–90% glycation of its otherwise free amino groups.

5. The viscoelastic preparation according to claim 4 wherein said glycated chitosan polymer possesses about 60% glycation of its otherwise free amino groups.

6. The viscoelastic preparation according to claim 1 wherein said glycated chitosan polymer has a molecular weight between 100,000 and 2,000,000 Daltons.

7. The viscoelastic preparation according to claim 1 comprising about nine percent by weight of said glycated chitosan polymer dispersed in said aqueous solution, wherein said glycated chitosan polymer possesses about 60% glycation of its otherwise free amino groups, and said aqueous solution having a viscosity of about 77,000 centistokes.

8. The viscoelastic preparation according to claim 1 additionally containing one or more different viscoelastic materials miscible in said aqueous solution.

9. The viscoelastic preparation according to claim 8 wherein said different viscoelastic material is selected from the group consisting of hyaluronic acid, chondroitin sulfate and carboxymethylcellulose.

10. The viscoelastic preparation according to claim 1 wherein said glycated chitosan polymer comprises a monosaccharide bonded to said otherwise free amino groups.

11. The viscoelastic preparation according to claim 10 wherein said monosaccharide comprises galactose.

12. The viscoelastic preparation according to claim 1 wherein said glycated chitosan polymer is in the form of a Schiff base, an Amadori product or mixtures thereof.

13. The viscoelastic preparation according to claim 1 wherein said glycated chitosan polymer is in the form of a reduced Schiff base, a reduced Amadori product or mixtures thereof.

14. The viscoelastic preparation according to claim 1 wherein said glycated chitosan polymer possesses a number of chemically modified monosaccharide or oligosaccharide substituents.

* * * * *

UNITED STATES PATENT AND TRADEMARK OFFICE
CERTIFICATE OF CORRECTION

PATENT NO. : 6,756,363 B1
APPLICATION NO. : 09/715429
DATED : June 29, 2004
INVENTOR(S) : Nordquist et al.

It is certified that error appears in the above-identified patent and that said Letters Patent is hereby corrected as shown below:

Col. 4, line 63, change "store" to -- stored --;

Col. 5, line 56 (in the diagram), change "NH" to -- $NH_2$ --;

Col. 5, line 61 (in the diagram), change "B(+) Galactose" to -- D(-) Galactose --;

Col. 5, line 50-65 for Exhibit A and Col. 6, line 1-21 for Exhibit B are attached and needs to be illustrated as shown, please insert;

Col. 6, line 8 (in the diagram), add -- HO -- to the left side;

Col. 6, line 8 (in the diagram), change "$H_2OH$" to -- H --;

Col. 6, line 14 (in the diagram), change "$H_2OH$" to -- H, OH --; and

Col. 8, line 16, change "CMC," to -- carboxy methyl cellulose, --.

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 6,756,363 B1
APPLICATION NO. : 09/715429
DATED : June 29, 2004
INVENTOR(S) : Nordquist et al.

It is certified that error appears in the above-identified patent and that said Letters Patent is hereby corrected as shown below:

Exhibit A

The Table under Example 4 of Col. 5 in USPN 6,756,363

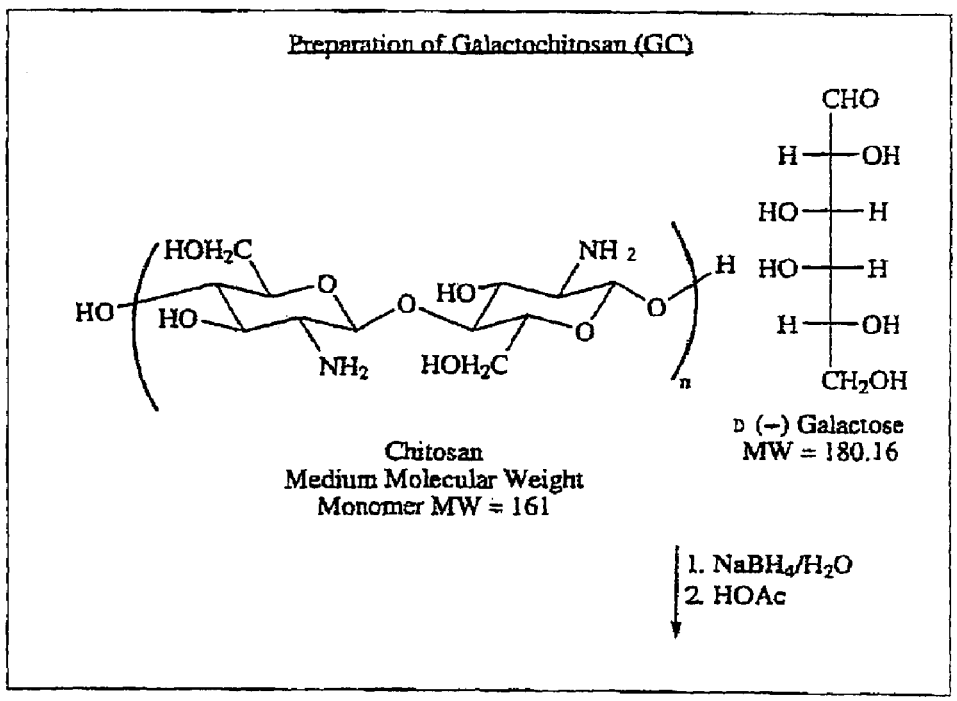

UNITED STATES PATENT AND TRADEMARK OFFICE
CERTIFICATE OF CORRECTION

PATENT NO.      : 6,756,363 B1
APPLICATION NO. : 09/715429
DATED           : June 29, 2004
INVENTOR(S)     : Nordquist et al.

It is certified that error appears in the above-identified patent and that said Letters Patent is hereby corrected as shown below:

Exhibit B

The Table continued under Example 4 of Col. 6 in USPN 6,756,363